US007740395B2

(12) United States Patent
Samuel et al.

(10) Patent No.: US 7,740,395 B2
(45) Date of Patent: Jun. 22, 2010

(54) ILLUMINATED AIR TREATMENT DEVICE

(75) Inventors: Jonathan Todd Samuel, West Chester, OH (US); Thomas Brian Norris, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/807,976

(22) Filed: May 31, 2007

(65) Prior Publication Data

US 2008/0298046 A1 Dec. 4, 2008

(51) Int. Cl.
*F21V 33/00* (2006.01)

(52) U.S. Cl. ....................... 362/643; 362/644; 362/101; 392/392; 392/395

(58) Field of Classification Search .................. 362/95, 362/96, 101, 641, 642, 643, 644; 392/392, 392/395
See application file for complete search history.

(56) References Cited

U.S. PATENT DOCUMENTS 6,478,440 B1 * 11/2002 Jaworski et al. ............... 362/96
6,859,615 B2 * 2/2005 Yip et al. .................... 392/395
7,357,561 B2 * 4/2008 Hidalgo et al. .............. 362/643
2005/0053368 A1 * 3/2005 Pesu et al. .................. 392/390
2006/0176693 A1 * 8/2006 Walter et al.
2007/0109782 A1 * 5/2007 Wolf et al.

FOREIGN PATENT DOCUMENTS

DE 103 49 559 A1 * 6/2005
WO WO 2007/035516 A2 * 3/2007
WO WO 2007/146370 A2 * 12/2007

OTHER PUBLICATIONS

International Search Report, mailed Oct. 29, 2008.*

* cited by examiner

*Primary Examiner*—Jacob Y Choi
(74) *Attorney, Agent, or Firm*—Larry L. Huston; Amy I. Ahn-Roll

(57) ABSTRACT

A light and air freshener in combination. The air freshener has one or more reservoirs which may be refilled or replaced. The light illuminates the reservoirs, to provide an aesthetically pleasing effect. The light may be specular and aimed towards a space between plural reservoirs. This arrangement provides the benefit that surface near the air freshener may be illuminated in an aesthetically pleasing manner while providing the functionality of a night light.

5 Claims, 4 Drawing Sheets

20
22
28
28
26
25
27
4
22
20
4
28

ILLUMINATED AIR TREATMENT DEVICE

FIELD OF THE INVENTION

The present invention relates to air treatment devices, such as air fresheners and more particularly to illuminated air fresheners.

BACKGROUND OF THE INVENTION

Volatile material-containing compositions are used for various purposes. Such purposes include, but are not limited to, releasing volatile materials such as perfumes, other scented materials, insecticides, air fresheners, deodorants, aromachology materials, aromatherapy materials, disinfectants, insect repellants or any other volatile that acts to condition, modify, or otherwise charge the atmosphere or to modify the environment. All are referred to herein as air freshening compositions.

Such air freshening compositions may be dispensed from an air treatment device, such as an air freshener. The air freshener may have a reservoir containing the air freshening composition. The reservoir may be illuminated for aesthetic or functional purposes.

The reservoir may be clear, allowing the user to know when the contents are depleted. The air freshener may be energized, as occurs with electric resistance heaters which increase the rate of volatilization of the air freshening composition. Alternatively, the air freshener may be passive and allow evaporation or sublimation to naturally occur, based upon ambient conditions.

Several air fresheners also incorporate illumination. The illumination may be provided by an incandescent light bulb, light emitting diode (organic or otherwise) (LED), an electroluminescent panel, (cold cathode or otherwise), EL film, fluorescent bulb, or a combination of more than one such sources. If desired, the light source may be disposed remote from the ultimate point of illumination and the light channeled to the area to be illuminated using a light channeling element such as fiber optics or other light pipes.

However, in the prior art attempts, such illumination may be aimed away from the reservoir and not adequately illuminate it, so that one cannot easily tell the state of reservoir in low light conditions, particularly if the reservoir contained a gel, darker contents or contents which closely matched the color of the walls of the reservoir. Or the illumination may be so diffuse, it is not helpful to function as a night light, in lieu of turning on a room light. Turning on the room light can awaken others sleeping nearby, which may be undesirable. Each of these prior art approaches does not solve the problem of providing convenient viewing of the reservoir in darkness or helping to identify any trip hazards in the vicinity of the air freshener without turning on room lights.

Yet another problem may occur when the air freshener is placed at a normal viewing level. For example, if the air freshener may be plugged into a wall outlet above a countertop and provided with illumination. If so, the prior art attempts are not always satisfactory. For example, the commercially available Glade PlugIns® device has a light which projects horizontally when in the normal usage position. If this device is used above a countertop, the light can be directed towards the users' eyes and be unpleasant. This arrangement defeats the intent of having a light which can create a calming effect. These problems, and others, are addressed by the present invention.

SUMMARY OF THE INVENTION

The invention comprises an air freshener and light therefor in combination. This combination comprises an air freshener delivery device having or being able to receive at least one reservoir for containing an air treatment therein, and a light for illuminating the air freshener delivery device. The light is specular and directed towards the reservoir. In a particular embodiment the invention may comprise an air freshener and light in combination having an air freshener delivery device with at least two spaced apart reservoirs, a directable light source whereby the light source can be directed in a path towards the space between the reservoirs, so that the light source can illuminate both said reservoirs or a portion of each reservoir. The path of the light may have a first end proximal to the light source and a distal end remote therefrom. The distal end of the light source is open, whereby light can be emitted from the path to illuminate a surface remote from the reservoirs and from the proximal end of the path.

Numerous other embodiments are also possible, including, but not limited to those described in the following detailed description. Further, all patents and applications cited herein are incorporated herein by reference.

DETAILED DESCRIPTION OF THE INVENTION

Figure 1:
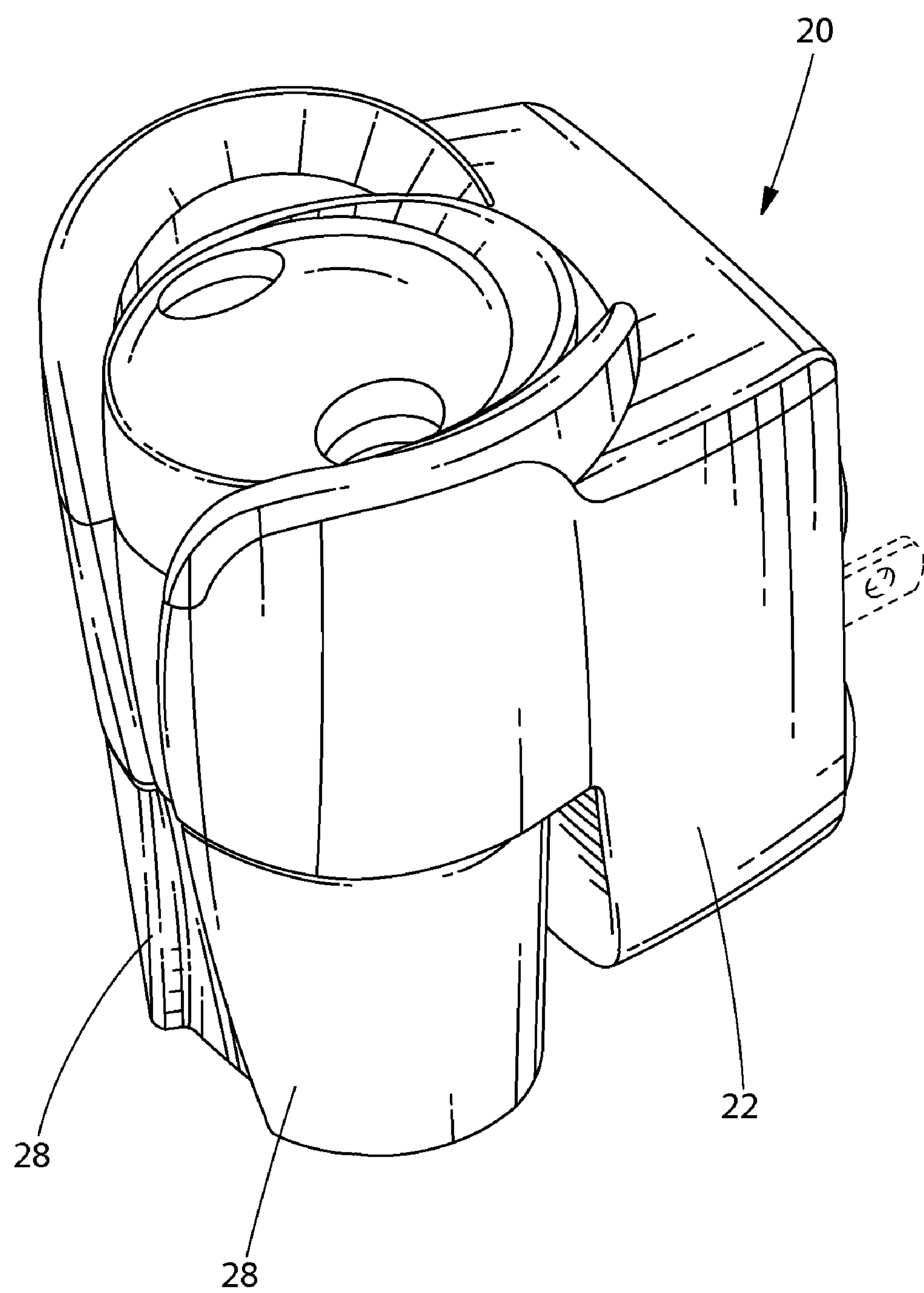
FIG. 1 is a perspective view of one non-limiting embodiment of a device according to the present invention.
Figure 2:
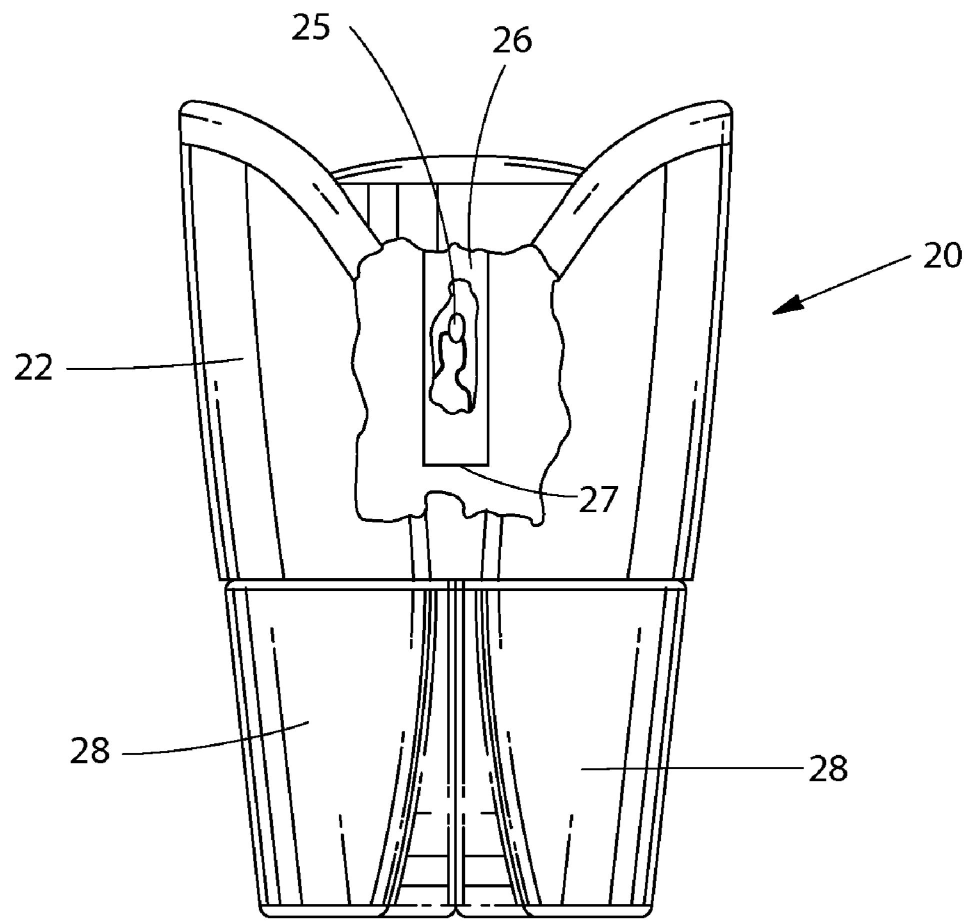
FIG. 2 is a frontal view of the device shown in FIG. 1 shown partially in cutaway.
Figure 3:
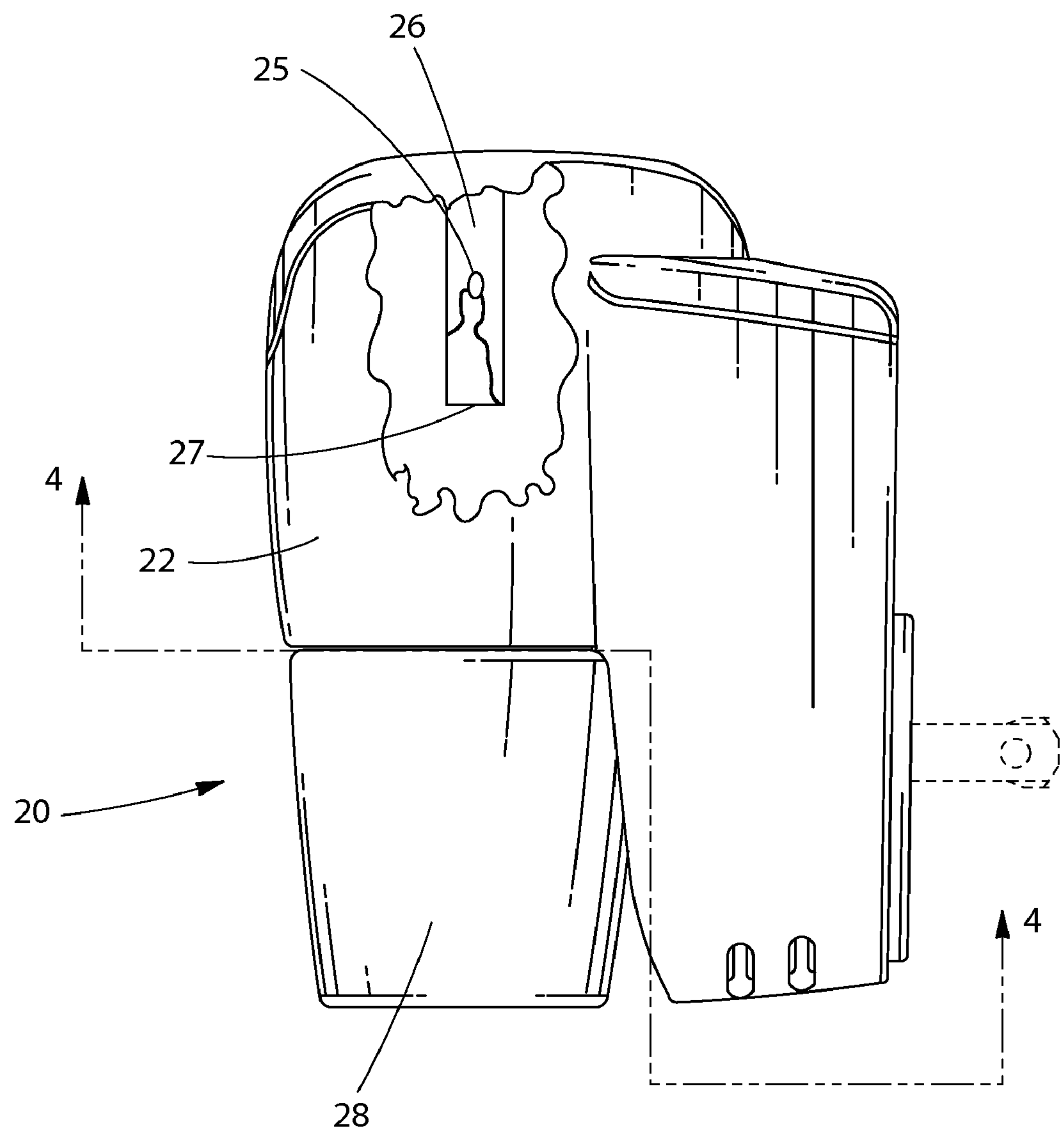
FIG. 3 is a side view of the device shown in FIG. 1, shown partially in cutaway.
Figure 4:
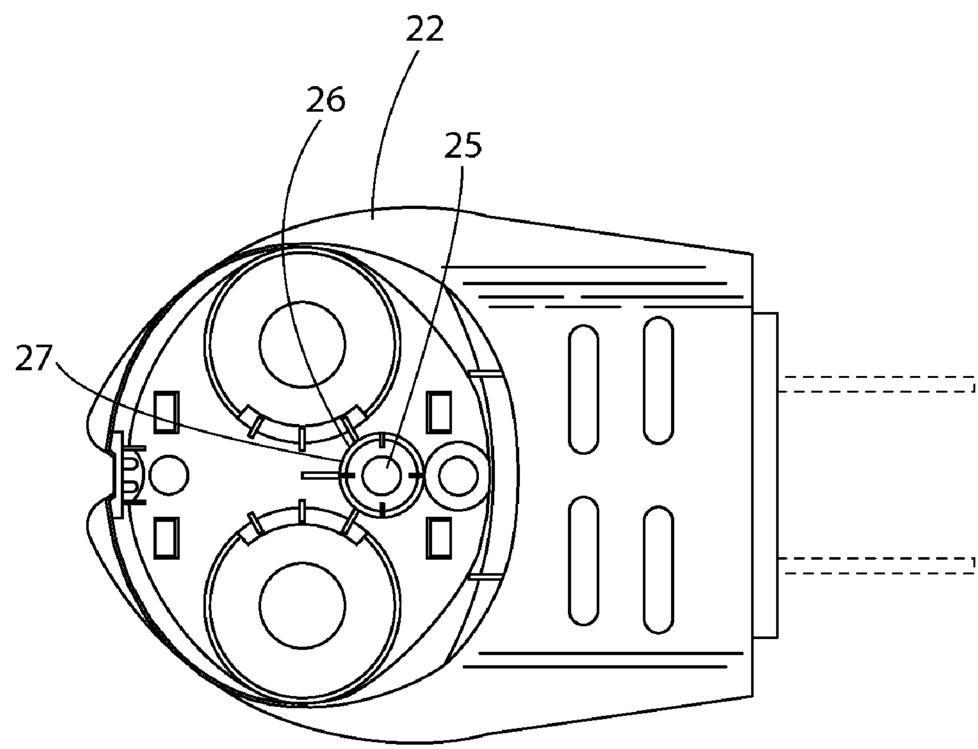
FIG. 4 is a cross-sectional view along lines 4-4 of the device shown in FIG. 3.

FIGS. 1-3 show an illustrative, non-limiting embodiment of a device 20 for emitting air freshening compositions according to the present invention. The device 20 may include or communicate with a power source to increase the delivery rate of volatile materials within the air freshening composition and an emission path. The emission path may include a wick, exit port, vent, etc.

The device 20 may comprise or be able to receive one or more reservoirs 28 for containing an air freshening composition, a connection to allow communication with a power source, and a delivery portion. As used herein, the condition of being able to receive a reservoir 28 includes the condition of actually comprising a reservoir 28, it being recognized that the reservoirs 28 may be permanently attached to or integral with a housing 22.

The device 20 may be provided with one or more air freshening compositions therein or the air freshening compositions may be later supplied. The one or more reservoirs 28 may be refillable or the reservoirs 28 may be disposed when the air freshening composition is depleted therefrom.

The device 20 may comprise a housing 22. The housing 22 may be supported by an electrical outlet through a plug that is at least indirectly connected to the housing 22. The reservoirs 28 can comprise any suitable type of container, and can be made of any suitable material. Suitable materials for the containers include, but are not limited to glass and plastic. The reservoirs 28 can comprise any type of leakproof container suitable for holding volatile materials. The reservoirs 28 may be part of the housing 22, or may be separate components removably attachable to a portion of the device 20 such as the housing 22. It is also possible for a single reservoir 28 to hold more than one type of air freshening composition. Such a reservoir 28 could, for instance, have two or more compartments for volatile materials.

The air freshening composition may be emitted in various facilities, which include but are not limited to homes, hospitals, offices, theaters, other buildings, the outdoors and the like, or into various vehicles such as trains, subways, automobiles, airplanes and the like or from computer systems. The air freshening composition may be emitted continuously or during discrete periods, at a single emission rate or a variable emission rate The air freshening composition may comprise a volatile material. The term "volatile material" as used herein, refers to a material that is vaporizable. The terms "volatile materials", "aroma", and "scents", as used herein, include, but are not limited to pleasant or savory smells, and also encompass scents that function as insecticides, air fresheners, deodorants, aromachology, aromatherapy, or any other volatile that acts to condition, modify, or otherwise charge the atmosphere or to modify the environment. It should be understood, however, that perfumes, aromatic materials, and scents will often be comprised of one or more volatile materials, which may form a unique and/or discrete unit comprised of a collection of volatile materials.

The volatile compositions described herein may also have non-volatile components. It should also be understood that when the volatile compositions are described herein as being "emitted", this refers to the volatilization of the volatile components thereof, and does not require that the non-volatile components be emitted.

The air freshening compositions of interest herein can be provided in any suitable form. In some embodiments, scents are provided by volatile compositions comprising perfume, such as perfume oils, that are incorporated onto or into a suitable carrier. The carriers can be provided in the following non-limiting forms: a solid, a liquid, a paste, a gel, beads, encapsulates, wicks, a carrier material, such as a porous material impregnated with or containing the perfume, and combinations thereof. In some embodiments, the carrier may be in the form of a pliable solid which can be melted and have the perfume ingredients added thereto in order to form a composition that is in the form of a pliable solid structure or matrix at room temperature (25° C., 50% RH).

In certain embodiments, the air freshening composition may have a viscosity of from about 1,000 Cps to about 1,000,000 Cps, or more, measured at a shear stress of 100 Pa in a rotational rheometer, like the AR2000 (TA instruments New Castle, Del., USA), using a 40-mm diameter cone-and-plate geometry at 25° C. Such a composition can exist as a gel up to at least about 13,000 Cps. In certain embodiments when the composition is in the form of a pliable solid, it may have a viscosity of from about 100,000 to about 1,000,000 Cps.

In one non-limiting embodiment, at room temperature the composition may be in the form of a structure that is a structured polymeric pliable solid. Such a structure may be porous or non-porous. The structure may be homogeneous (which may also be referred to herein as "continuous"), or non-homogeneous. The structure may be permeable to volatile materials contained therein. This will allow the structure to release the volatile materials contained therein when desired. The composition may comprise a non-porous, homogeneous, permeable, structured polymeric pliable solid.

The structure (or matrix) comprising the air freshening composition can be thermally triggered or otherwise energized to emit the volatile material(s) and volatile dye(s). The thermal energy may be electrically supplied, such as from a DC or AC source, including a battery or wall outlet. The device 20 may be provided with an adapter so that it can be plugged into the cigarette lighter of a vehicle. The device 20 may be provided with a remote control that allows the user to control any, or all, of the emission properties of the device 20 (including, but not limited to changing the volatile material being emitted) without touching the device 20.

The device 20 can have a pre-selected emission program which is already programmed when a consumer buys the device 20, or the device 20 can be provided with a selection of several emission programs and the consumer can select between these programs. In these or other embodiments, the device 20 can use technology similar to the "random play" technology used in compact disc (CD) players to randomly alternate between different volatile materials.

The device 20 may be configured to turn on and off in response to stimuli, such as light, noise and/or motion. For example, the device 20 may be programmed to turn on when it senses light, and another device 20 may be programmed to turn off when it senses light. A microprocessor can be used with motion sensors to turn on the device 20 or a component thereof, for example, a heater, light source 25 and/or a fan in the device 20 singularly or in any combination. The device 20 can be off until the time until a person moves in the vicinity of the motion sensor, when it is activated to provide air freshening.

A programmable microprocessor may provide flexibility in controlling the characteristics of the emission of the volatile materials. The microprocessor, heater, light source 25 and any circuit board therefore may be wired in series to provide a reasonably simple construction.

There need not be a separate energy source, or volatilization source for each air freshening composition. A single energy source, such as a heater can be supplied for multiple reservoirs 28. There can be any suitable number of volatilization sources for the volatile compositions. For example, a single volatilization source can be used to volatilize more than one volatile composition. Such a volatilization source could, for example, be capable of moving to volatilize the different volatile compositions, or it can be capable of selectively directing energy (e.g., heat) to the different volatile compositions (such as by opening and closing a door or gate between a volatilization source and a given volatile composition). Alternatively, reservoirs 28 can be movable relative to the volatilization source so that the reservoirs 28 can be selectively moved relative to a heater, for example. The device 20 may comprise at least one heating system or heater, such as resistance heaters 40, 42. For example, the heaters may comprise resistance heating elements in the form of rings that at least partially surround the wicks protruding from the reservoirs 28.

The device 20 may comprise one or more aromatic material-containing reservoirs 28, which may be provided in the form of fragrance cartridges. Each cartridge may provide a single volatile composition, or a combination of different volatile materials, such as a combination of different scented materials. In certain embodiments, each of plural cartridges may provide a collection of scents that conveys, e.g., a theme, an experience, a physiological effect, and/or a therapeutic effect.

The reservoirs 28 may further comprise a seal 36 for containing the volatile material, and a wick 38 for dispensing the volatile material. The device 20 and/or the reservoir 28 may further comprise an additional seal for covering the wick 38 of one or more of the volatile materials when the volatile material is not being emitted.

The device 20 may also be sold in the form of a kit that includes the device 20 and one or more reservoirs 28 of air freshening compositions. The device 20 and/or kit can also include instructions for use which instruct the user regarding certain emission periods that may be used to produce desired results, and/or instructions regarding how to use the device 20.

The light source 25 used herein may be specular or diffuse. By specular it is meant that the light has a focus in a particular direction. Such focus and directionality may be inherent to the light source 25 or provided by collimating the light, by the use of lenses, mirrors, prisms, or other optical elements. By diffuse it is meant that the light may be emitted in any, even if some directionality occurs incidental to reflection off various surfaces external to the light and its intended path.

The light from the light source 25 may be collimated using a tube or any other subtractive collimator 26. The collimator 26 may be a tube of any desired cross section, with a constant cylindrical cross section being shown. A variable cross section of any other suitable shape may be used as well. The collimator may have a proximal end juxtaposed with the light source 25 and a distal end 27 remote therefrom. The distal end 27 of the collimator 26 may be open to allow light to travel in a specular manner and in a particular direction from the collimator 26. Light may travel from the light source 25 through the distal end 27 of the collimator 26. By changing the direction of the collimator 26, the direction of the travel of the light may be changed. This arrangement allows the light to be directional, as well as specular, using a single collimator 26.

If specular, the light source 25 may be aimed downwardly. This directionality allows the light emitted from the light source 25 to illuminate the floor near device 20, minimizing trip hazards or a countertop if the device is used in a kitchen.

If the device 20 is plugged directly into a wall outlet, as opposed to being connected via a cord, the light may also illuminate part of the wall and reflect therefrom. The device 20 may illuminate surfaces in its proximity such as wall, floor, countertops, etc. This reflection may also provide illumination for trip hazards, etc.

The specular light source 25 may be mounted to be aimed towards the reservoir 28. If multiple reservoirs 28 are used, the reservoirs 28 may be spaced apart. By spaced apart it is meant that the reservoirs 28 do not share a common wall and that a visually discernable space occurs between the reservoirs 28, although the space may be interrupted by one or more struts, septums or other connections between the reservoirs 28.

The light source 25 may be aimed at the space between the reservoirs 28. For example, the light source 25 may be mounted above the reservoirs 28 and aimed downwardly towards the reservoirs 28 or a void space therebetween. In another embodiment the light source 25 may be mounted below the reservoirs 28 and aimed upwardly or a void space therebetween, or may be mounted lateral to one or more reservoirs 28 and aimed transversely thereto or a void space therebetween.

Aiming the specular light from the light source 25 towards the reservoirs 28 provides another benefit. Particularly, indirectly illuminating the reservoirs 28 by aiming the light source 25 therebetween may provide greater consumer acceptance than a diffuse light or a light that is aimed away from the reservoirs 28.

The reservoir may be opaque, translucent or transparent. A transparent or translucent reservoir provides the benefit that a calming effect may occur when the reservoir 28 is indirectly illuminated by light from the light source 25. This effect may be enhanced when the light source 25 is not aimed directly at the reservoir 28, but instead when the light only has indirect contact therewith. For example, if the light source 25 is aimed downwardly when the device 20 is in the normal usage position, the light may illuminate nearby surface, functioning as a nightlight, concurrently illuminate the reservoir(s) 28 and not be aimed towards the users' eye should the device 20 be plugged into an outlet above a countertop or otherwise used above waist-high elevation.

The light source 25 may be disposed external to the reservoir and illuminate the reservoir, and its contents, from outside the reservoir. Alternatively, the light source 25 may be disposed internal to the reservoir. This arrangement provides the advantage that a calming glow may occur, as seen through the liquid composition.

The light source 25 may have an intensity of at least 6,000, 7,000, 8,000, 9,000 or 10,000 mcd. If an LED is selected for the light source 25, the LED may be driven at less than full brightness, and may be used at approximately 80% of rated brightness value. This intensity is believed to be adequate to illuminate the reservoirs 28 and the surroundings. The intensity may be less than 15,000, 14,000, 13,000, 12,000 or less than 11,000 mcd, so as not to be obtrusive. The color may be defined by a CIE 1931 Chromaticity Coordinate x of 0.2 to 0.4 with a range of 0.25 to 0.30 having been found suitable, and may also have a CIE 1931 Chromaticity Coordinate y ranging from 0.2 to 0.4 with a range of 0.23 to 0.30 having been found suitable. The LED may have a color variation of plus, or minus 25% and be used with a current of approximately 20 mA, to dissipate approximately 0.07 Watt or less.

While prior art nightlights used bulbs of 4 to 7 watts, such a relatively large wattage may overwhelm the heater, if present, dedicated to a particular reservoir 28. This situation may render a dedicated heater, having a typical wattage of about 1 watt, ineffective for timed release of an air freshening composition from that reservoir 28. Thus, instead of providing the perception of alternating fragrances sourced from different alternating heated reservoirs 28, excessive heat from the light source 25 may cause the perception of blending of plural fragrances. To avoid this situation the light source 25 may be designed to dissipate less wattage the heater, for a particular reservoir 28.

The light source 25 may have an included angle of less than 45, 30, 15 or 10 degrees. A smaller included angle may provide the benefit of more focus and greater light illuminating one or more surfaces external to the device 20.

If the device 20 utilizes plural reservoirs, 28, the reservoirs 28 may be disposed in symmetrical relationship, as illustrated. For example, the reservoirs 28 may be of identical size and shape. As viewed from the top, two reservoirs 28 may be disposed at 180 degree intervals, three reservoirs 28 may be disposed at 120 degree intervals, etc.

The light source 25 may be mounted between the reservoirs 28 and aimed at the space separating the reservoirs 28. This arrangement provides generally equal and isomeric illumination of both reservoirs 28, which has been found to be consumer preferred, it being recognized that differences in the coloration or quantity of air freshening composition within the reservoirs 28 may affect the perception of the degree of illumination.

While equally spaced, sized and balanced reservoirs 28 are illustrated herein the invention is not so limited. For example, a reservoir 28 which responds more brightly to illumination from the light source 25 may be placed from the one viewing the device 20 than a reservoir 30 which responds less brightly to the illumination. The result yields a desirable effect of equal illumination.

If the reservoirs 28 are separated by a septum or other connection, the light source 25 may be aimed at the directly septum, illuminating it. This arrangement allows the light to indirectly and equally illuminate two, three, four or more reservoirs 28 equilaterally joined to the septum. The septum may be made of the same material as the reservoirs 28 or may be made of any suitable material which transmits/reflects light from the source to the proximal walls of the reservoirs 28.

The shortest distance between the closest portion of adjacent reservoirs 28 is referred to as the spacing distance. The spacing distance should allow the specular light to hit and reflect from the walls of the reservoirs 28. This geometry allows a downwardly oriented light to illuminate the reservoir 28 walls for aesthetic effect and concurrently illuminate the floor or countertop for functional effect.

The device 20 is not limited to a single light source 25. Plural light sources 25 may be utilized. Equivalent light sources 25 may be utilized and equally spaced from equivalently illuminatable reservoirs 28. Alternatively, brighter light sources(s) 25 may be utilized in conjunction with a reservoir (s) 28 which responds more darkly to illumination from the light source 25. The light source 25 may be spaced relatively closer to/further from a reservoir 28 which responds less/more to the illumination, respectively.

If desired, the device 20 may be provided with plural reservoirs 28 and a corresponding number of plural light sources 25. Each such light source 25 may be dedicated to or directed towards a corresponding reservoir 28. As a particular reservoir 28 is heated, the corresponding light source 25 may be activated, illuminating that particular reservoir 28. This arrangement alerts the consumer to which reservoir 28 is active at any particular point in time.

If desired the CIE 1931 chromatic coordinates may be adjusted to the materials of adjacent reservoirs 28 if the reservoirs 28 are not made of like materials, or any of these variations may be used in combination with other variations. The device 20 may also contain a component, such as a fan, for diffusing or transporting the volatile materials into the environment or atmosphere The heater and fan may work simultaneously, in sequence or a combination thereof.

The device 20 may further comprise a switching mechanism that changes the volatile material being emitted by the device 20. The switching mechanism can comprise any suitable type of mechanism that causes the device 20 to change the volatile material being emitted. In the embodiment shown, the switching mechanism controls the activation of the heaters so that the heater will be turned on for the volatile material which is desired to be emitted. Suitable switching mechanisms include, but are not limited to: analog timing circuitry, digital circuitry, combinations of analog and digital circuitry, microprocessors, and mechanical actuation switches such as shape memory alloys (NiTi wire) or bimetallic switches. Alternative types of switching mechanisms include: (1) a magnetic sensor with a pickup that counts the number of rotations of the motor of a fan, or the fan itself, used to disperse the volatile composition(s) such that after a certain number of rotations, the device 20 will switch from one volatile composition to another; and (2) a device 20 comprising dual shape memory alloys, or bimetallic strips or switches that can complete a circuit at ambient temperature and then cut-off when a certain temperature is reached. The two-way effect can be used so that as the temperature is reduced, the material can complete the circuit again, thus acting as a thermostat to keep the heater on and then turn it off. The shape memory alloy may serve as the heater as well as the pulse generator.

The device 20 may optionally be provided with indicators so that a user is aware that the volatile material being emitted has changed. Such indicators can be visual and/or audible. For example, in the case of scented materials, such an indicator may allow a person to see which scent is being emitted at a given time. At least a portion of the device 20 (such as all or a portion of the housing) or the containers may be made of a type of plastic that changes color when heated.

The device 20 may be provided with additional user controls, such as an "on/off" switch to allow a user to turn the device 20 on and off without removing it from the electrical socket or other power source. The device 20 can be provided with a control that allows the user to control the emission period of the volatile materials, and/or the time between the emission of the different volatile materials, or the time that the volatile materials are emitted during an overlapping time period. For example, in one non-limiting embodiment, if the device 20 is provided with the capability of emitting each volatile material during a period greater than 15 minutes and less than or equal to 24 hours, then the device 20 can be provided with a control that allows the user to set the emission period to 72 minutes, or to one hour, for example.

Suitable air freshener devices 20 may be made in accordance with the teachings of commonly assigned US patent applications 2004/002855A1; 2006/108803A1; 2004/0033171 A1; 2005/0201944 A1; 2004/0265164 A1; and/or Ser. No. 11/216,618. It should be understood that every maximum numerical limitation given throughout this specification will includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

What is claimed is:

1. An air freshener and light therefor in combination comprising:

an air freshener device able to receive at least two spaced apart, transparent reservoirs for containing an air freshening composition therein;

a light source for illuminating said air freshener device, wherein said light source is specular and is disposed in a collimator having a constant cross section, a first end proximal to said light source and a distal end remote therefrom, said distal end of said light source being open, and is aimed downwards towards a space between said reservoirs, and wherein said light source dissipates approximately 0.7 Watts or less.

2. An air freshener and light according to claim 1 wherein said light has a CIE 1931 Chromaticity coordinate x ranging from 0.2 to 0.4, and a CIE 1931 Chromaticity coordinate y ranging from 0.2 to 0.4.

3. An air freshener and light according to claim 2 wherein said light has an intensity of at least 10,000 mcd.

4. An air freshener and light according to claim 1 wherein said reservoirs are disposed in symmetrically opposite relationship.

5. An air freshener and light according to claim 4 wherein said reservoirs are spaced apart by a septum.

* * * * *